United States Patent [19]

Okumura et al.

[11] 4,099,054
[45] Jul. 4, 1978

[54] SEM HAVING D-C BIAS OF VIDEO SIGNAL CONTROLLED BY MAXIMUM AND/OR MINIMUM OF CRT BEAM CURRENT

[75] Inventors: Masahide Okumura, Katsuta; Yasushi Saito, Mito, both of Japan

[73] Assignee: Hitachi, Ltd., Japan

[21] Appl. No.: 810,163

[22] Filed: Jun. 27, 1977

Related U.S. Application Data

[63] Continuation of Ser. No. 631,720, Nov. 13, 1975, abandoned.

[30] Foreign Application Priority Data

Nov. 20, 1974 [JP] Japan ................. 49-132759

[51] Int. Cl.² ............................................. G01N 23/00
[52] U.S. Cl. ..................... 250/306; 250/311; 315/383
[58] Field of Search ............... 250/306, 311, 309, 310; 315/383

[56] References Cited

U.S. PATENT DOCUMENTS 3,072,741  1/1963  Ahrons et al. ............... 315/383

*Primary Examiner*—Alfred E. Smith
*Assistant Examiner*—T. N. Grigsby
*Attorney, Agent, or Firm*—Craig & Antonelli

[57] ABSTRACT

A charged particle apparatus wherein a charged particle beam irradiates an object to be observed and secondary emissions such as secondary electrons thus emitted from a surface layer of the object are detected. A signal indicative of the detected secondary emissions is applied to a control grid of a cathode ray tube to modulate an electron beam irradiating a fluorescent screen thereof. A detector detects the electron beam intensity of the cathode ray tube and minimum and maximum or peak values of the detected electron beam intensity are compared with predetermined reference signals to obtain deviation signals indicative of the difference therebetween. The signal applied to the control grid of the cathode ray tube is controlled in accordance with the deviation signals.

17 Claims, 1 Drawing Figure

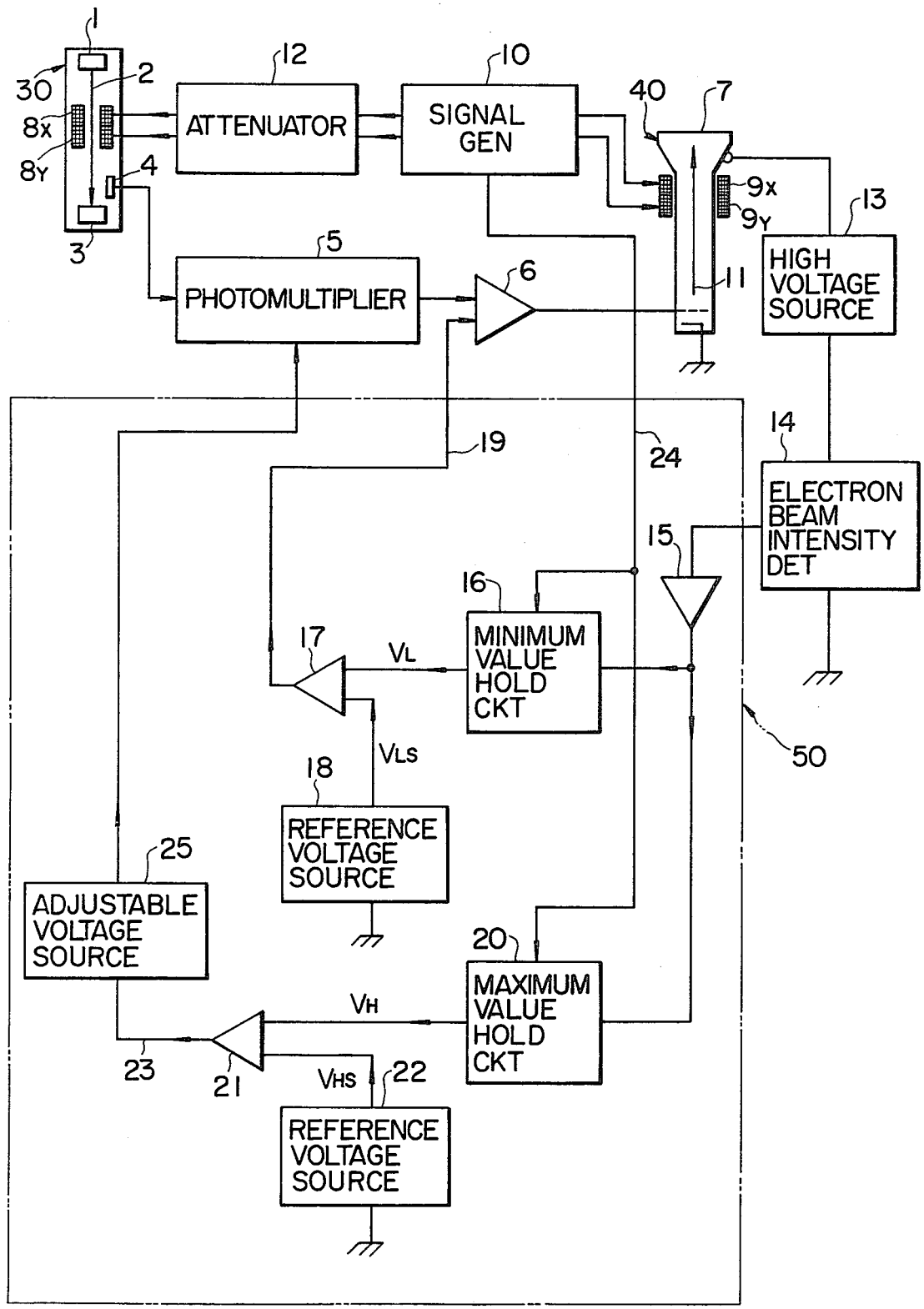

SEM HAVING D-C BIAS OF VIDEO SIGNAL CONTROLLED BY MAXIMUM AND/OR MINIMUM OF CRT BEAM CURRENT

This is a continuation of application Ser. No. 631,720 filed Nov. 13, 1975 and now abandoned.

BACKGROUND OF THE INVENTION

1. Field of the Invention

This invention relates to improvements in apparatus for microanalysis, by utilizing a charged particle beam as a probe such as an electron beam or an ion beam, and more particularly to a scanning electron microscope which is provided with a control circuit for adjusting the contrast and brightness of an image or a picture representative of a surface layer of an object to be observed.

2. Description of the Prior Art

For the purpose of microanalysis, an apparatus utilizing a charged particle beam, such as an X-ray microanalyzer, Auger electron microanalyzer and scanning electron microscope is frequently used. This invention is applicable to all the abovementioned apparatus, however, for the sake of explanatory convenience, a description will be made hereafter in terms of the scanning electron microscope.

With the scanning electron microscope, a surface layer of an object to be examined is irradiated and two-dimensionally scanned with an electron beam focussed at a microregion on the object. Secondary electrons thus emitted from the surface layer are detected and amplified by means of a photo-multiplier and then applied to a control grid of a cathode ray tube so that an electron beam irradiating a fluorescent screen can be modulated.

When both the electron beams irradiating the object and the fluorescent screen are two-dimensionally scanned in synchronism, the view or condition of the surface layer can be observed as an enlarged image or picture on the fluorescent screen.

In order to obtain the best quality and the emphasized contrast of the enlarged image, a video signal applied to the control grid of the cathode ray tube is required to have a D.C. level and a maximum amplitude just within the operating range of the cathode ray tube. That is, the video signal, D.C. level which corresponds to the brightness in the darkest portion on the object, is selected by adjusting the bias voltage of the video amplifier, to have a value corresponding to an electron beam intensity equal to or slightly higher than an intensity at a rising part of the brightness-beam intensity characteristic of the fluorescent screen.

Also, the maximum amplitude of the video signal, which represents brightness in the brightest portion of the object, is adjusted by controlling the gain of the video signal to a value corresponding to an electron beam intensity being equal to or slightly lower than the value at the beginning of a saturating part of the brightness-beam intensity characteristic.

These adjustments are very troublesome and time consuming since they are frequently required at, for example, a time when it is necessary to change the intensity of an electron beam irradiating an object or when it is necessary to examine various kinds of objects.

To eliminate such disadvantages, one type of apparatus has been proposed in which a detector is provided for detecting the minimum and maximum values of a video signal to be applied to a control grid of a cathode ray tube. In response to the thus detected signals, the bias voltage and the gain of a video amplifier are automatically controlled so as to maintain the D.C. level and the peak value of the video signal at predetermined levels.

However, this improved apparatus still has disadvantages such as deteriorated quality of the image or the picture showing the object because of fluctuations or changes in the beam emission characteristics and the operating voltage of the cathode ray tube. That is, even though the peak value of the video signal is fixed at a predetermined value, the electron beam intensity often exceeds the value at which the brightness of the image or the picture is saturated if the electron emission efficiency from a gun is increased. In this case, the brightest portion of the object cannot be observed in detail.

On the other hand, when the emission efficiency is decreased, the intensity of the electron beam is often less than the value at a rising part of the brightness-beam intensity characteristic of the fluorescent screen, so that the darkest portion of the object cannot be observed in detail.

SUMMARY OF THE INVENTION

The primary object of the present invention is to provide an improved charged particle device such as an electron microscope and related equipment in which the above-mentioned disadvantages of the prior art devices are eliminated.

In particular, it is an object of the present invention to provide a scanning electron microscope able to display an image showing an object with predetermined contrast and the predetermined darkest or brightest level.

To accomplish this object, the present invention is characterized in that a detector is provided for detecting the intensity of an electron beam flowing towards a fluorescent screen of a cathode ray tube.

According to a feature of the present invention, a control circuit is provided for maintaining the minimum and maximum values of the detected signal and for controlling the bias voltage and the gain of a video amplifier in response to signals stored in a holding means.

Other objects and features of the present invention will become apparent from the following detailed description taken in conjunction with the accompanying drawing.

BRIEF DESCRIPTION OF THE DRAWING

The single FIGURE is a block diagram showing an embodiment of the present invention.

PREFERRED EMBODIMENT OF THE INVENTION

In the FIGURE, an electron beam 2 emitted from an electron gun 1 of a charged particle device such as an electron microscope 30 irradiates an object 3 to be examined or observed.

Secondary electrons are thus emitted from the surface layer of the object 3 and detected by a detector 4 such as a photoscintillator. The output of the detector 4 is amplified by a photomultiplier 5 and an amplifier 6, and then applied to a control grid of a cathode ray tube 40. The electron microscope 30 and the cathode ray tube 40 are provided with deflecting coils 8x, 8y and 9x, 9y, respectively, to which saw-tooth current is supplied from a signal generator 10 to scan the electron beams in the X- and Y-directions. Both the electron beams irradiating the object 3 and the fluorescent screen of the cathode ray tube 40 are two-dimensionally scanned in synchronism.

A variable attenuator 12 connected across the sawtooth generator 10 and the deflecting coils 8x, 8y serves to adjust the extent of the area to be scanned with the electron beam 2 so that an enlarged view or condition of the surface layer of the object can be observed with an arbitrary multiplication ratio.

The electron beam 11 of the cathode ray tube 40 is modulated in response to the video signal applied to its control grid and then accelerated through an electric field formed by an acclerating voltage source 13 which is connected across an acclerating electrode (not shown) and a ground. The thus accelerated electron beam impinges on the fluorescent screen 7 of the cathode ray tube 40 and brightens it in response to the intensity of the beam current. That is, the electron beam intensity determines the brightness of the image or picture on the fluorescent screen 7.

This electron beam current flows through a closed loop including the acclerating voltage source 13 and the cathode ray tube 40. Therefore, the beam intensity can be detected by means of a detector 14 inserted at any place in this loop, for example connected across the high voltage source 13 and ground. The detector 14 may be a resistor connected between the voltage source 13 and ground, across which a voltage drop can be extracted.

The output of the electron beam intensity detector 14 is amplified by an amplifier 15 and then applied to both minimum and maximum value hold circuits 16 and 20.

The minimum value hold circuit 16 serves to detect the D.C. bias level of the video signal and maintains it during the period of one frame of the image of the picture. The D.C. signal charged on the hold circuit 16 is renewed once every one frame of the image by a pulse supplied from the signal generator 10 through a line 24.

The output $V_L$ of the hold circuit 16 is applied to a differential amplifier 17 to be compared with a reference voltage $V_{LS}$. The reference voltage $V_{LS}$ from a voltage source 18 is adjusted to a predetermined value which corresponds to the minimum beam intensity required for exciting the fluorescent screen and brightening it.

The difference or deviation between the voltages $V_L$ and $V_{LS}$ are amplified and then applied through a line 19 to the amplifier 6 so as to control the bias voltage thereof. A closed loop comprising the amplifier 6, the cathode ray tube 40, the beam current detector 14, the amplifier 15, the minimum value hold circuit 16 and the differential amplifier 17 forms a negative feedback circuit which serves to enable the deviation voltage $(V_{LS}-V_{LS})$ to become zero. Consequently, the brightness of the darkest portion of the image displayed by the cathode ray tube 40 can be maintained at a predetermined level.

On the other hand, the maximum value hold circuit 20 serves to detect the beam current peak and hold it during the period of one frame of the image of the picture. The thus detected peak is applied to a differential amplifier 21 to be compared with a reference voltage $V_{HS}$, which is supplied from a voltage source 22. This voltage $V_{HS}$ is set in advance at a predetermined value corresponding to the maximum electron beam intensity at which the brightness of the image is not saturated. The output of the differential amplifier 21 is supplied through a line 23 to a variable votage source 25 which delivers a control voltage to be applied to the photomultiplier 5. Another negative feedback circuit is thus formed by a closed loop including the photomultiplier 5, the amplifier 6, the cathode ray tube 40, the detector 14, the amplifier 15, the maximum hold circuit 20, the differential amplifier 21 and the adjustable voltage source 25, which functions to enable the deviation voltage $(V_H-V_{HS})$ to become zero.

According to the present invention, the minimum beam intensity corresponding to the D.C. bias level of the video signal and the maximum beam intensity corresponding to the peak of the video signal are always fixed at predetermined values regardless of fluctuations or variations in the display characteristics of the cathode ray tube and changes in various kinds of voltages to drive the cathode ray tube and the electron microscope. Thus, the view or condition of the surface layer of the object can be observed with an enlarged image or picture whose contrast and brightness at the darkest or brightest portion are maintained constant.

Although only a single specific embodiment of the invention has been shown and described, it will be appreciated that it is only illustrative and that various modifications may be made without departing from the spirit of this invention. For instance, instead of the photomultiplier for amplifying detected electrons, a secondary electron multiplier or a combination of a Faraday cup an amplifier may be used.

As the apparatus utilizing a charged particle beam as a probe, many other equipments such as X-ray microanalyzer, Auger electron microanalyzer, and ion microanalyzer is well known and frequently used for the purpose of microanalysis. In such microanalyzer, when an object to be examined is irradiated with said charged particle beam (such as electron beam or ion beam), secondary emissions (such as X-rays, Auger electrons and secondary ions) are emanated from said object. Then by detecting and analyzing said secondary emissions, certain informations concerning said object are obtained. Although foregoing embodiment has been shown in term of only the scanning electron microscope, this invention is applicable to all of the above mentioned apparatus utilizing a charged particle beam as a probe.

We claim:

1. A charged particle apparatus comprising:

means for irradiating and two-dimensionally scanning an object to be observed with a primary charged particle beam;

means for detecting secondary emission particles emitted from a surface layer of the object and providing a first output signal indicative thereof;

cathode ray tube means having a control grid responsive to the first output signal for displaying an image of the object in accordance therewith, said cathode ray tube means having an electron beam two-dimensionally scanned in synchronism with the primary charged particle beam;

means for detecting the intensity of the electron beam current of the cathode ray tube means which irradiates a fluorescent screen of said cathode ray tube means; and means for controlling the first output signal in response to the intensity of the electron beam current detected by said intensity detecting means, including first means for detecting and holding a minimum value of the detected electron beam current, means for comparing the minimum value of the detected electron beam current with a first predetermined reference value and for providing a first deviation signal indicative of the difference therebetween, means for adjusting the D.C. bias of the first output signal of the secondary detecting means in accordance with the first deviation signal so that the minimum value of the electron beam current is substantially equal to the first reference value, second means for detecting and holding a peak value of the electron beam current detected by said intensity detecting means, means for comparing the peak value with a second predetermined reference value and for providing a second deviation signal indicative of the difference therebetween, and means for adjusting the amplitude of the first output signal of said secondary detecting means so that the peak value is substantially equal to the second predetermined reference value, said secondary emission particle detecting means including a detector providing an output indicative of secondary emissions to a first amplifying means providing an amplified output to a second amplifying means providing an amplified output to the control grid of said cathode ray tube means, said first amplifying means also receiving the second deviation signal and said second amplifying means receiving the first deviation signal.

2. An apparatus according to claim 1, wherein said first amplifying means includes a photomultiplying means.

3. In a charged particle beam apparatus having means for irradiating an object to be observed with a primary charged particle beam, a cathode ray tube having an electron beam irradiating a fluorescent screen thereof, means for scanning said primary charged particle beam and said electron beam in synchronism, means for detecting secondary emission particles emitted from said object, and means for amplifying the output signal of said detecting means to form a video signal modulating the electron beam current of said cathode ray tube, the improvement comprising means for detecting the minimum value of the electron beam current of said cathode ray tube during one video frame, and means for controlling the D.C. bias of said video signal in response to the minimum value detected during said video frame.

4. A charged particle beam apparatus according to claim 3, wherein said controlling means includes means for storing the detected minimum value during said video frame, means for comparing the stored value with a reference value and means for adjusting the D.C. bias of said video signal in response to the output signal of said comparing means.

5. A charged particle beam apparatus according to claim 4, further including means for resetting said storing means once during each video frame.

6. In a charged particle beam apparatus having means for irradiating an object to be observed with a primary charged particle beam, a cathode ray tube having an electron beam irradiating a fluorescent screen thereof, means for scanning said primary charged particle beam and said electron beam in synchronism, means for detecting secondary emission particles emitted from said object, and means for amplifying the output signal of said detecting means to form a video signal modulating the electron beam current of said cathode ray tube, the improvement comprising means for detecting the maximum value of the electron beam current of said cathode ray tube during one video frame, and means for controlling the gain of said amplifying means in response to the maximum value detected during said video frame.

7. A charged particle beam apparatus according to claim 6, wherein said controlling means includes means for storing the detected maximum value during said video frame, means for comparing the stored value with a reference value and means for adjusting the gain of said amplifying means in response to the output signal of said comparing means.

8. A charged particle beam apparatus according to claim 7, further including means for resetting said storing means once during each video frame.

9. In a charged particle beam apparatus having means for irradiating an object to be observed with a primary charged particle beam, a cathode ray tube having an electron beam irradiating a fluorescent screen thereof, means for scanning said primary charged particle beam and said electron beam in synchronism, means for detecting secondary emission particles emitted from said object, and means for amplifying the output signal of said detecting means to form a video signal modulating the electron beam current of said cathode ray tube, the improvement comprising means for detecting the minimum and maximum values of the electron beam current of said cathode ray tube during one video frame, means for controlling the D.C. bias of said video signal in response to the minimum value detected during said video frame, and means for controlling the gain of said amplifying means in response to the maximum value detected during said video frame.

10. A charged particle beam apparatus according to claim 9, wherein said D.C. bias controlling means includes means for storing the detected minimum value during said video frame, first means for comparing the stored minimum value with a first reference value and means for adjusting the D.C. bias of said video signal in response to the output signal of said first comparing means, and said gain controlling means includes means for storing the detected maximum value during said video frame, second means for comparing the stored maximum value with a second reference value and means for adjusting the gain of said amplifying means in response to the output signal of said second comparing means.

11. A charged particle beam apparatus according to claim 10, further including means for resetting said storing means once during each video frame.

12. In a charged particle beam apparatus having means for irradiating an object to be observed with a primary charged particle beam, a cathode ray tube having an electron beam irradiating a fluorescent screen thereof, means for scanning said primary charged particle beam and said electron beam in synchronism, means for detecting secondary emissions from said object, and means for amplifying the output signal of said detecting means to form a video signal modulating the electron beam current of said cathode ray tube, the improvement comprising means for detecting the intensity of the electron beam current of said cathode ray tube, means for detecting and holding the minimum value of the detected electron beam current intensity during the period of one video frame, and means for controlling the D.C. bias of said video signal in response to the held minimum value.

13. A charged particle beam apparatus according to claim 12, wherein said controlling means includes means for comparing the held minimum value with a reference value and means for adjusting the D.C. bias of said video signal in response to the output signal of said comparing means.

14. A charged particle beam apparatus according to claim 12, further including means for resetting said detecting and holding means once during each video frame.

15. In a charged particle beam apparatus having means for irradiating an object to be observed with a primary charged particle beam, a cathode ray tube having an electron beam irradiating a fluorescent screen therof, means for scanning said primary charged particle beam and said electron beam in synchronism, means for detecting secondary emissions from said object, and means for amplifying the output signal of said detecting means to form a video signal modulating the electron beam current of said cathode ray tube, the improvement comprising means for detecting the intensity of the electron beam current of said cathode ray tube, means for detecting and holding the minimum value of the detected electron beam current intensity during the period of one video frame, means for detecting and holding the maximum value of the detected electron beam current intensity during the period of one video frame, means for controlling the D.C. bias of said video signal in response to the held minimum value, and means for controlling the amplitude of said video signal in response to the held maximum value.

16. A charged particle beam apparatus according to claim 15, wherein said D.C. bias controlling means includes first means for comparing the held minimum value with a first reference value and means for adjusting the D.C. bias of said video signal in response to the output signal of said first comparing means, and wherein said amplitude controlling means includes second means for comparing the held maximum value with a second reference value and means for adjusting the gain of said amplifying means in response to the output signal of said second comparing means.

17. A charged particle apparatus according to claim 15, further including means for resetting said detecting and holding means once during each video frame.

* * * * *